United States Patent [19]
Lefrancier et al.

[11] Patent Number: 4,693,998
[45] Date of Patent: Sep. 15, 1987

[54] NOVEL COMPOUNDS OF THE MURAMYL PEPTIDE

[75] Inventors: Pierre Lefrancier, Bures Sur Yvette; Monique Parant, Paris; Francoise Audibert, Neuilly Sur Seine; Louis Chedid; Jean Choay, both of Paris; Edgar Lederer, Sceaux, all of France

[73] Assignee: Agence Nationale de Valorisation de la Rechersche, France

[21] Appl. No.: 797,771

[22] Filed: Nov. 7, 1985

Related U.S. Application Data

[63] Continuation of Ser. No. 391,140, Jun. 23, 1982, , Continuation of Ser. No. 131,138, Mar. 17, 1980, , Continuation of Ser. No. 045,401, Jun. 14, 1979.

[30] Foreign Application Priority Data

Jun. 5, 1978 [FR] France .................. 79 16793

[51] Int. Cl.$^4$ .................... A61K 31/70; C07H 5/04
[52] U.S. Cl. ............................ 514/62; 536/55.2
[58] Field of Search ................. 530/322; 424/89; 514/62; 536/55.2

[56] References Cited

U.S. PATENT DOCUMENTS 4,153,684  5/1979  Audibert et al. .......... 260/112.5 R

FOREIGN PATENT DOCUMENTS 849214  12/1976  Belgium .
2015534   9/1979  United Kingdom .

OTHER PUBLICATIONS

Kusumoto et al., *Chemical Abstract*, 89, 215758(b), (1978).
Adams et al., *Bichem. Biophy. Comm.* 72(1), 339–346 (1976).
Kotani et al., *Biken Journal*, 18, 105–111, (1975).
Chedid et al., *Proc. Natl. Acad. Sci.*, 75, 2472–75 (1976).

*Primary Examiner*—Delbert R. Phillips
*Attorney, Agent, or Firm*—Weiser and Stapler

[57] ABSTRACT

The compounds have the structure 2-(2-amino or alkylamido-2-desoxy-3-O-D-glucopyranosyl)-alkanyl-dipeptide, possibly substituted on the saccharide residue the amino acid residue at the end of the peptide chain being a D-glutamyl residue whose α-carboxy function is esterified and γ-carboxyl function amidated. The compounds are valuable as immunological medicaments.

20 Claims, No Drawings

NOVEL COMPOUNDS OF THE MURAMYL PEPTIDE

This application is continuation of Ser. No. 391,140, filed June 23, 1982 now abandoned, which in turn is a continuation of Ser. No. 131,138, filed Mar. 17, 1980 now abandoned, which in turn is a continuation of Ser. No. 045,401, filed June 14, 1979 now abandoned.

The invention relates to novel compounds of the 2-(2-acetamido-2-desoxy-3-0-D-glucopyranosyl)-alkanyl-peptide, which compounds are endowed with biological and pharmacological properties of great value. More particularly, the invention concerns among these compounds those which possess immunoregulator properties notably non-specific immunological adjuvants, these compounds being suitable among other activities, for reinforcing the immunoprotector activity of immunogenic agents of all types, natural or synthetic.

The invention relates also to the uses to which the compounds, according to the present patent application, are capable of giving rise, as well as to the particular compositions containing such compounds, more particularly suitable for the practicing of these uses.

It relates also to biological reactants, for example standard immunological adjuvants, which can be constituted by means of the compounds according to the invention, notably in order to study the possible adjuvant properties of substances for investigation by comparison with such standard adjuvants or, on the other hand, as an agent capable of countering certain effects connected with the administration of immunosuppressor substances.

The invention relates more particularly again to the application of the compounds concerned to the amplification of the immunogenic effect of active principles of vaccines administered to an animal or human host.

Consequently, the invention relates also again to pharmaceutical compositions whose active principle is constituted by at least one of the compounds defined below, in association with the pharmaceutical vehicle suitable for the mode of administration required or useful having regard to the nature of the vaccinating principle used.

Of course considerable efforts have been devoted for a long time to research for agents endowed with adjuvant properties of the type recalled above. For a long time, these research efforts have borne on natural extracts, such as can be obtained from bacteria, notably mycobacteria. Although it has thus been possible to obtain products which were highly active and having reached a high degree of purification, decisive progress has been accomplished by the development of series of smaller molecules, from now on accessible to chemical synthesis. One of the most representative compounds of this series is constituted by 2-(2-acetamido-2-desoxy-3-0-D-glucopyranosyl)-D-propionyl-L-alanyl-D-isoglutamine, also named more simply N-acetyl-muramyl-L-alanyl-D-isoglutamine, of the formula

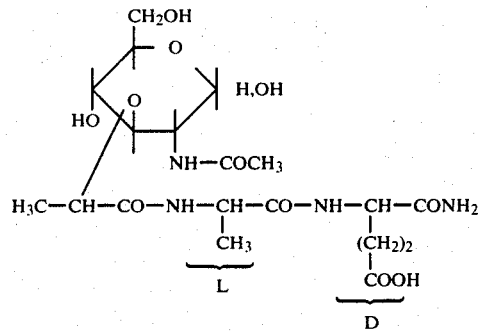

(This compound was the subject of French Patent Application No. 74 22090 and notably of a corresponding application in the U.S. Pat. No. 516,991 of 22/10/1974)

Thus it has been possible to obtain series of compounds devoid of the well known toxic effects caused by immunostimulants and whose immunological adjuvant activity, very powerful for certain among them, is manifested when these compounds are administered to a host, even in the absence of any oily support, as was hitherto necessary to enable the manifestation of the immunological adjuvant properties of the natural extracts, notably obtained from mycobacteria.

Studies conducted on these series of compounds have permitted the observation that modification or substitution of certain functional groups belonging to various parts of the molecule, for example the replacement of the first amino acid residue of the peptide chain in N-acetyl-muramyl-L-alanyl-D-isoglutamine, could be carried out without the adjuvant activity of the initial compound being lost.

Thus, the adjuvant activity can be preserved on replacement of the propionyl group, substituting the 2 position of the glucopyranosyl residue by another group of alkanyl type at the corresponding place in the molecule. Finally, the first aminoacyl residue, namely L-alanyl, can be replaced by other aminoacyl residues, such as glycyl or preferably L-seryl. It is also possible to replace it by another aminoacyl residue such as for example L-prolyl, L-threonyl or L-valyl.

On the other hand, other parts of the molecule cannot be modified profoundly without the adjuvant activity of the whole of the molecule then being lost, at least to a great extent. In this regard, the presence in the peptide chain of a group derived from glutamic acid, as the second aminoacyl residue of the chain, is up to now critical for the maintenance of the adjuvant activity. In addition, it is accepted that the compounds very active as immunological adjuvants are those for which the α-carboxylic group of the glutamic residue has been converted into an amide group when they are used in the form of water-in-oil emulsion. The importance of the carboxamide configuration of the α-carboxylic group of the glutamic residue has been stressed by various authors. In this respect, one may, for example, recall the observations of Arlette ADAM et coll. (Biochemical & Biophysical Research Communications, Vol. 72, No. 1, 1976) which have for example established the lesser adjuvant activity in oil of the dimethyl ester of N-acetyl-muramyl-L-alanyl-D-glutamic acid (which shows, in addition, other biological properties of greater interest) than that of the γ-methyl ester of N-acetyl-muramyl-L-alanyl-D-isoglutamine.

Similar observations have been made by a Japanese research team, as is again observed, for example, in the publication of Shozo KOTANI et coll. (Biken Journal, Vol. 19, 9–13, 1976).

The compounds already described in the state of the art, among which the glutamic residue is α-carboxamidated, are however capable of presenting in vivo a certain pyrogenic effect, notably when they are administered at high doses. Studies carried out in this field by various teams have shown that there exists an apparent correlation between the adjuvant effect of the most active substances and their possible pyrogenicity under certain experimental conditions. Shozo KOTANI et coll. have offered the hypothesis that this pyrogenicity could possibly be attributed to the relationship between the compounds studied and the peptidoglycan fragments which can be obtained from gram positive bacteria (in the publication already mentioned above).

These authors formulate the hypothesis that there could exist a possible relationship between the mecanisms taking place at the level of the immune response of mammifers, under the effect of antigenic stimulation, and those taking place at the level of the regulation of the temperature of the body or of the febrile response. They offer also the idea that certain targets of N-acetyl-muramyl-peptides are involved in the two mecanisms. In fact, these authors have observed that, among the compounds which they have tested, the most adjuvant were also the most pyrogenic, and that on the contrary the less adjuvant were also the least pyrogenic.

This rule has not in fact been really shown to be faulty up to the present, even if certain products already described show a very low level of pyrogenicity at the doses and under the experimental conditions. It is thus, for example, with the diamide of N-acetyl-muramyl-L-alanyl-D-glutamic acid. However, this product, if it possesses a particularly favorable therapeutic index, is albeit less active than N-acetyl-muramyl-L-alanyl-D-isoglutamine.

The development of research in this particular field of the technique, which has led to the novel compounds which are the subject of the present patent application, has enabled a certain number of surprising conclusions to be arrived at. In fact, it is possible to obtain very powerful adjuvant compounds, including a single amide function substituting the γ-carboxylic group of the glutamic residue of the derivatives of the type concerned, on condition however that the α-carboxylic group of the glutamic residue be also substituted in predetermined manner, this adjuvant activity being capable of being manifested both in aqueous solution and in water-in-oil emulsion. This result is all the more unexpected as it is well known that N-acetyl-muramyl-L-alanyl-D-glutamine (including therefore an amide function on the carboxylic group at the γ of the glutamyl group) is only very slightly adjuvant in vivo, when it is administered in the form of a water in oil emulsion.

Similarly, the apparent correlation which has been observed between the adjuvant and pyrogenic actions of known compounds is from now on seriously questionable by the experimental results obtained within the scope of the present invention. This is particularly the case thus with the compounds according to the invention of which certain are characterized by a degree of apyrogenicity hitherto never achieved.

These observations apply to the products according to the invention which, like those in the prior art, are constituted by a compound of the type 2-(2-amino- or acyl-amido-2-desoxy-3-0-D-glucopyranosyl)-alkanyl-peptide having, if necessary, the substitutions and replacements which have been evoked above, these products being nonetheless characterized by the simultaneous presence of an amide function (—CONH$_2$) on the γ-carboxylic group and of an ester function on the α-carboxylic group of the glutamic residue.

The invention relates notably to the novel compounds responding to the general formula

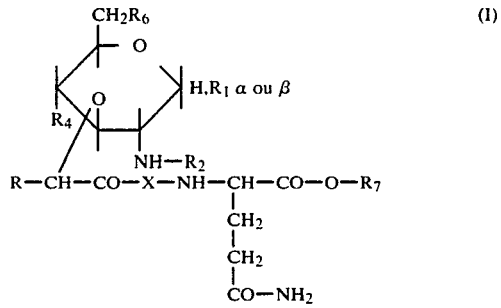

$$R-CH-CO-X-NH-CH-CO-O-R_7$$
$$\qquad\qquad\qquad\qquad\qquad |$$
$$\qquad\qquad\qquad\qquad\quad CH_2$$
$$\qquad\qquad\qquad\qquad\quad |$$
$$\qquad\qquad\qquad\qquad\quad CH_2$$
$$\qquad\qquad\qquad\qquad\quad |$$
$$\qquad\qquad\qquad\qquad\quad CO-NH_2$$

in which the substituents R, R$_1$, R$_2$, R$_4$, R$_6$, R$_7$, X have the following significances:

R is either a hydrogen atom, or an alkyl group comprising 1 to 4 carbon atoms,

R$_1$ is either —NH$_2$, or —OH, or a radical resulting from the substitution of a hydrogen of one or the other of these functions by an alkyl, or aryl, or alkyl-aryl radical, having at the most 10 carbon atoms, which can bear functional groups, notably aminophenyl, R$_2$ is a hydrogen atom or an acyl radical which can carry functional groups and including at the most 22 carbon atoms, and preferably from 1 to 4 carbon atoms, R$_4$ is a hydroxyl or the group resulting from the substitution of the hydrogen of the hydroxyl by an acyl or alkyl radical comprising at the most 4 carbon atoms, R$_6$ is either —NH$_2$, or —OH, or the group resulting from the substitution of a hydrogen of one of these functions by an acyl or alkyl radical, saturated or not, possibly branched, substituted or not, containing from 1 to about 90 carbon atoms, and which can, in addition, carry functional groups: hydroxyl, carboxyl, carbonyl, amino, cyclopropane, methoxy, X is one of the aminoacyl residues L-alanyl, L-arginyl, L-lysyl, L-asparagyl, L-aspartyl, L-cysteinyl, L-glutaminyl, L-glutamyl, glycyl, L-histidyl, L-hydroxyprolyl, L-isoleucyl, L-leucyl, L-methionyl, L-phenylalanyl, L-prolyl, L-seryl, L-threonyl, L-tryptophanyl, and L-valyl, R$_7$ is a linear or branched alkyl residue, saturated or not, which can carry functional groups, an aryl or alkyl-aryl residue, possibly substituted, and comprises at the most 10 carbon atoms.

Among the compounds of the general formula I, certain are particularly advantageous. Below are indicated the different significances of the variable elements of formula I corresponding to preferred structures.

In this formula, the second aminoacyl group of the peptide chain linked to the muramyl type residue is D-glutamyl residue. The first aminoacyl group (denoted by X) can, on the other hand, be selected from among the various aminoacyl residues mentioned above. Among the compounds of formula I, those are preferred in which the first aminoacyl residue in L-alanyl. A second type of preferred compound in that in which this aminoacyl is L-seryl. Another type of preferred compound is that in which this aminoacyl is glycyl.

Also advantageous are the compounds in which the first aminoacyl residue in L-prolyl, L-threonyl or L-valyl.

The group at the α position of the D-glutamyl residue is preferably a carbon chain ester comprising from 1 to 4 carbon atoms.

A preferred form is constituted by the case where $R_7$ is either $-CH_3$, or $-C_2H_5$ or $-C_3H_7$.

Another preferred form is constituted by the compounds in which the $R_7$ radical comprises 4 carbons.

In the most usual preferred form, that is to say that for which the structure of muramic acid is to be found, R is $-CH_3$. In another preferred form, the R group is hydrogen; the structure is then that of the homologue denoted by the name nor-muramic acid. Finally, in another preferred form, R is $-C_2H_5$; to this form corresponds the so-called homo-muramic structure.

The glycoside linkage of the saccharide portion in the products according to the invention can be presented in α or β anomer forms. The oside residue can also receive different substituents of which the prior art, relating to adjuvant agents of the muramyl peptide type, has given a certain number of examples on the hydroxyl functions which can be esterified or etherified and on the amine function at the 2 position which can be acylated.

In the general formula of the products according to the invention, the substituents of the glucopyranoside ring have been denoted by $R_1$, $R_2$, $R_4$, and $R_6$. The various positions do not have the same possibilities of substitution, the 6 position being that for which the greatest latitude is offered.

The preferred compounds are those for which 1 or several of the substituents $R_1$, $R_4$ and $R_6$, independently of one another or simultaneously, are a hydroxyl.

Advantageous compounds are also those for which $R_4$ corresponds to mono-succinic or acetic esters.

The preferred compounds are those for which $R_6$ is an amine function, or again an ester, of which the acyl residue contains from 1 to 6 carbon atoms, in particular the acetic or mono-succinic esters. $R_6$ is also advantageously the ester corresponding to mycolic acids (about $C_{80}$ to $C_{90}$) or corynomycolic acid ($C_{32}$).

In the preferred compounds, $R_2$ is an acetyl group ($-CO-CH_3$) or a hydrogen.

Preferred compounds according to the invention are the methyl, ethyl, propyl, hexyl and decyl esters of N-acetyl-muramyl-L-alanyl-D-glutamine. A particularly preferred compound in the butyl ester of N-acetyl-muramyl-L-alanyl-D-glutamine.

Other preferred compounds are those of formula I in which the various substituents correspond to those given in the following table.

| $R_1$ | $R_2$ | $R_4$ | $R_6$ | R | X | $R_7$ |
|---|---|---|---|---|---|---|
| OH | COCH$_3$ | OH | OH | CH$_3$ | L-Ala | C$_2$H$_5$ |
| " | " | " | " | " | Gly | CH$_3$ |
| " | " | " | " | " | " | C$_4$H$_9$ |
| " | " | " | " | " | " | C$_6$H$_{13}$ |
| " | " | " | " | " | " | C$_{10}$H$_{21}$ |
| " | " | " | " | " | L-Ser | CH$_3$ |
| " | " | " | " | " | " | C$_4$H$_9$ |
| " | " | " | " | " | " | C$_6$H$_{13}$ |
| " | " | " | " | " | " | C$_{10}$H$_{21}$ |
| " | " | " | " | " | L-Val | CH$_3$ |
| " | " | " | " | " | " | C$_4$H$_9$ |
| " | " | " | " | " | " | C$_6$H$_{13}$ |
| " | " | " | " | " | " | C$_{10}$H$_{21}$ |

-continued

| $R_1$ | $R_2$ | $R_4$ | $R_6$ | R | X | $R_7$ |
|---|---|---|---|---|---|---|
| " | " | " | " | H | L-Ala | CH$_3$ |
| " | " | " | " | " | " | C$_4$H$_9$ |
| " | " | " | " | " | " | C$_{10}$H$_{21}$ |
| " | " | " | " | " | Gly | CH$_3$ |
| " | " | " | " | " | " | C$_4$H$_9$ |
| " | " | " | " | " | " | C$_{10}$H$_{21}$ |
| " | " | " | " | " | Ser | CH$_3$ |
| " | " | " | " | " | " | C$_4$H$_9$ |
| " | " | " | " | " | " | C$_{10}$H$_{21}$ |
| " | " | " | " | " | Val | CH$_3$ |
| " | " | " | " | " | " | C$_4$H$_9$ |
| " | " | " | " | " | " | C$_{10}$H$_{21}$ |
| " | " | " | " | C$_2$H$_5$ | L-Ala | CH$_3$ |
| " | " | " | " | " | " | C$_4$H$_9$ |
| " | " | " | " | " | " | C$_{10}$H$_{21}$ |
| " | " | " | Corynomycoloyl | CH$_3$ | " | CH$_3$ |
| " | " | " | " | " | " | C$_4$H$_9$ |
| " | " | " | " | " | " | C$_{10}$H$_{21}$ |
| " | " | " | " | " | Ser | CH$_3$ |
| " | " | " | " | " | " | C$_4$H$_9$ |
| " | " | " | " | " | " | C$_{10}$H$_{21}$ |
| " | " | " | " | H | L-Ala | CH$_3$ |
| " | " | " | " | " | " | C$_4$H$_9$ |
| " | " | " | " | " | " | C$_{10}$H$_{21}$ |
| " | " | " | Mycoloyl | CH$_3$ | " | CH$_3$ |
| " | " | " | " | " | " | C$_4$H$_9$ |
| " | " | " | " | " | " | C$_{10}$H$_{21}$ |
| " | " | " | " | " | Ser | CH$_3$ |
| " | " | " | " | " | " | C$_4$H$_9$ |
| " | " | " | " | " | " | C$_{10}$H$_{21}$ |
| " | " | " | " | H | L-Ala | CH$_3$ |
| " | " | " | " | " | " | C$_4$H$_9$ |
| " | " | " | " | " | " | C$_{10}$H$_{21}$ |
| C$_6$H$_4$—NH$_2$ | " | " | OH | CH$_3$ | " | CH$_3$ |
| " | " | " | " | " | " | C$_4$H$_9$ |
| " | " | " | " | " | " | C$_{10}$H$_{21}$ |
| " | " | " | " | H | " | CH$_3$ |
| " | " | " | " | " | " | C$_4$H$_9$ |
| " | " | " | " | " | " | C$_{10}$H$_{21}$ |
| OH | " | OCH$_3$ | OH | CH$_3$ | " | CH$_3$ |
| " | " | " | " | " | " | C$_4$H$_9$ |
| " | " | " | " | " | " | C$_{10}$H$_{21}$ |
| " | " | " | " | " | L-Ser | CH$_3$ |
| " | " | " | " | " | " | C$_4$H$_9$ |
| " | " | " | " | " | " | C$_{10}$H$_{21}$ |
| " | " | OH | OCH$_3$ | " | L-Ala | CH$_3$ |
| " | " | " | " | " | " | C$_4$H$_9$ |
| " | " | " | " | " | " | C$_{10}$H$_{21}$ |
| " | " | " | " | " | L-Ser | CH$_3$ |
| " | " | " | " | " | " | C$_4$H$_9$ |
| " | " | " | " | " | " | C$_{10}$H$_{21}$ |
| " | " | OCH$_3$ | " | " | L-Ala | CH$_3$ |
| " | " | " | " | " | " | C$_4$H$_9$ |
| " | " | " | " | " | " | C$_{10}$H$_{21}$ |
| " | " | " | " | " | L-Ser | CH$_3$ |
| " | " | " | " | " | " | C$_4$H$_9$ |
| " | " | " | " | " | " | C$_{10}$H$_{21}$ |
| " | " | OH | " | " | L-Ala | CH$_3$ |
| " | " | " | " | " | " | C$_4$H$_9$ |
| " | " | " | " | " | " | C$_{10}$H$_{21}$ |
| " | " | " | OC$_{10}$H$_{21}$ | " | " | CH$_3$ |
| " | " | " | " | " | " | C$_4$H$_9$ |
| " | " | " | " | " | " | C$_{10}$H$_{21}$ |
| " | " | " | " | " | L-Ser | CH$_3$ |
| " | " | " | " | " | " | C$_4$H$_9$ |
| " | " | " | " | " | " | C$_{10}$H$_{21}$ |
| " | " | " | C$_4$H$_5$O$_4$ | " | L-Ala | CH$_3$ |
| " | " | " | " | " | " | C$_4$H$_9$ |
| " | " | " | " | " | " | C$_{10}$H$_{21}$ |
| " | " | " | " | " | L-Ser | CH$_3$ |
| " | " | " | " | " | " | C$_4$H$_9$ |
| " | " | " | " | " | " | C$_{10}$H$_{21}$ |

The products according to the invention are prepared by synthesis, certain of the compounds used in these syntheses being obtainable from natural products.

The synthesis of these molecules of a glycopeptide nature, of which the sequence comprises a dipeptide residue fixed to N-acetyl-muramic acid residue, or an analogue or derivative of the latter such as indicated above, is produced according to the methods used conventionally in peptide or saccharide synthesis. Such methods have been amply described in the prior art, as well as in French patent applications, notably Nos. 76 06820, 76 06821, 76 21889 and 77 02646.

These syntheses can be done by coupling a derivative of muramic acid or an analogue of the latter, either successively with a derivative of the first amino acid, then of the second amino acid, or with a dipeptide derivative, the temporary protection groups being finally removed. In a modification, these syntheses lead to the production of glycopeptide derivatives whose carboxylic function is free and can then be substituted by an ester group ($R_7$). The choice of the reaction sequence is guided principally by reasons of convenience, of yield and of production of homogenous products, notably stereochemically.

Below are given succinctly the principal indications relating to various operations which can be applied for synthesizing the products corresponding with formula I, first envisaging each step separately, then indicating some preferred type reaction sequences.

(1) Preparation of muramic acid, its analogues or their derivatives

The preparation of such products can be done from compounds described in prior publications. If necessary, for those whose preparation does not appear expressly in the literature, they can be obtained according to the methods for preparing the corresponding derivatives, used conventionally in oligosaccharide chemistry.

(a) Preparation of muramic acid or its analogues

To obtain the analogues of N-acetyl-muramic acid of the formula

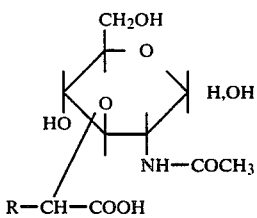

in which R has the previously indicated significance, it is possible to start with a derivative of N-acetyl-glucosamine when hydroxyls in 1, 4 and 6 position are blocked conventionally. A mode of preparing such a derivative, the benzyl-2-acetamido-4,6-O-benzylidene-2-deoxy-D-glucopyranoside, is described notably by P. H. GROSS and R. W. JEANLOZ (J. Org. Chem. 1967, 32, 2761).

The formation of N-acetyl-muramic acid ($R=CH_3$) or of one of its analogues can be carried out in the manner described in French Patent Application No. 74 22909 or 76 19236 (respectively, for these applications, $R=CH_3$ and $R=H$) taking up again the method described by OZAWA and JEANLOZ (J. Org. Chem., 1965, 30, 448).

This formation comprises, for example, the preparation of a sodium salt of the hydroxyl at the 3 position and the subsequent condensation of the sodium derivative with the salt or the ester of an α halogenated acid such as chloro-2-propionic or chloroacetic acids to take up the case again of the two previously indicated patent applications. The halogen compound used of form L can be prepared by the method described by SINAY et al (J. Biol. Chem., 1972, 247, 391). Using suitable halogen acids, it is possible to prepare all the derivatives corresponding to the various significances of R. Thus, to introduce an R group with 2 carbons, there may be used the salts or esters of chloro-2-butyric acid.

When a halogenated acid ester is used, in order to be able to proceed with the subsequent peptide condensation, the carboxylic function can be freed by suitable hydrolysis.

(b) Substitution on the saccharide residue

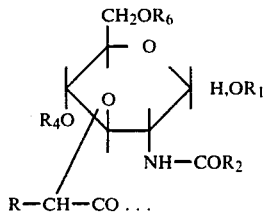

Starting from the N-acetyl-muramic derivatives blocked in the 1, 4, 6 positions as obtained in (a), it is possible to prepare the various analogous compounds in which the acetyl group fixed to the nitrogen at the 2 position is replaced by the substituents of which the nature is that given in the general definition, that is to say an acyl group including at the most 22 carbon atoms. For this modification, it is possible to operate in known manner by hydrolysis of the acetyl with a strong base, for example, as described in the publication of P. H. GROSS and R. W. JEANLOZ indicated above.

The resulting compound, in which an amino group is in the 2 position of the glucopyranoside ring, can then again be subjected to acylation, under the usual conditions, with a suitable acylating agent corresponding to the group $R_2$ that it is desired to introduce. As acylating agent, it is possible to use notably the acid anhydrides or chlorides.

The substitutions at the 1, 4 and 6 position can be carried out by methods which have been described previously and which are conventional in sugar chemistry. When the substituents envisaged are different from one another, as many successive substitution reactions are followed as there are separate substituents. In the course of these reactions, the positions which do not have to be substituted or those which must subsequently be the subject of another substitution are protected temporarily by blocking groups by the the usual methods.

The blocking groups initially present, in the case where one starts, as previously indicated, with benzyl-2-acetamido-4,6,-O-benzylidene-2-deoxy-D-glucopyranoside, are removed for example by the action of acetic acid (60% 1 hour reflux) and catalytic hydrogenation, as described for example by MERSER et al (Biochem. Biophys. Res. Commun., 1974, 466, 1316), or by catalytic hydrogenation as described for example by LEFRANCIER et al. (Int. J. Peptide Protein Res., 1977, 9, 249).

The methods of substitution are those conventionally used. To obtain the acylated derivatives, procedure is by means of an acylating agent corresponding to the substituent that it is desired to introduce (anhydride, acyl chloride, etc.).

The 1, 4, 6 positions are not equivalent as regards their activity. The $C^6$ position is the easiest to substitute, also, when only this position has to be substituted, it is possible to operate without blocking the other positions, with an amount of substituting agent equivalent to that necessary for the substitution of a single position.

A particular example of the method of preparing derivatives substituted at the 6 position is given in the article of KUSUMOTO et al. (Tetrahedron Letters, 1976, 47, 4237).

The substitutions on the oside residue can be carried out before or after the fixing of the peptide chain or of the fragments of the latter.

(2) Preparation of the peptide chain

The synthesis of the dipeptide residue is carried out according to conventional methods of peptide synthesis. By way of example, it is possible to use the activation methods of carboxyls, like the so-called method of mixed anhydrides. Advantageously, the peptide synthesis is carried out by means of a compound of the carbodiimide type such as N,N'-dicyclo-hexylcarbodiimide or equivalent carbodiimides. A review of the traditional methods of peptide synthesis will be found in J. H. JONES, Chemistry and Industry, 723 (1974). It is also possible to refer to the already mentioned French patent applications, or again to the following applications: Nos. 75 29624, 76 06819, 76 06820, 7606821, 76 21889, 77 02646, and to the article of LEFRANCIER et al (Int. J. Peptide Protein Res., 1977, 9, 249).

The substitutions of the carboxyl function of the D-glutaminyl residue by an ester group ($R_7$) are advantageously carried out on a derivative of D-glutamine, before its coupling with a derivative of L-alanine. However, it may also be advantageous to operate this substitution on a dipeptide derivative. In both cases, the reaction is effected, for example, according to the technique described by WANG et al. (J. Org. Chem., 42(1977), 1286).

Synthesis sequences of glycopeptides of formula I

The starting material is a derivative (1), $R_1$ representing a benzyl glycoside radical, prepared as described by GROSS and JEANLOZ (J. Org. Chem., 1967, 32, 2759). To obtain the similar compound in which $R_1$ is a group other than benzyl, it is possible to use the method of preparation of α or β-glucosides described in this same article, or any known method for such preparations in oligosaccharide chemistry.

To modify the nature of the N-acyl group at the 2 position, the N-acetyl group can be hydrolysed as described by GROSS and JEANLOZ (J. Org. Chem., 1967, 32, 2759) to end up with derivatives of formula (2). These derivatives may be selectively N-acylated, notably by the action of the anhydride of a carboxylic acid, to result in derivatives of formula (3). In a preferred modification, the newly introduced acyl group (thus the benzyloxycarbonyl group) may be selectively removed in the final stage of the synthesis thus freeing the amine function. The derivatives of formula (4) may be obtained from the foregoing ones according to the method described by OZAWA and JEANLOZ (J. Org. Chem., 1965, 30, 448), by means of a chloroacetic acid, or more generally of an L-α-chloroalkanoic acid.

The derivatives of formula (4) can be coupled with a dipeptide derivative of the general formula H-X-D-Glu($NH_2$)-O-$R_7$ hydrochloride.

These various peptide derivatives are prepared according to the methods described by LEFRANCIER et al. (Int. J. Peptide Protein Res., 1977, 9, 249; 1978, 11, 289, and 1979 submitted for publication).

The coupling methods used to obtain the glycopeptide derivatives of formula (5) are also described in the previously cited articles. However, both in the synthesis of the dipeptide derivatives and in that of the derivatives of formula (5), any coupling method may be used.

Catalytic hydrogenation of the compounds of formula (5) is carried out conventionally (LEFRANCIER et al., 1977, reference cited) to result in compounds of formula (6).

In a modification, the derivatives of formula (5) undergo selective debenzylidenation such as described by MERSER et al. (Biochem. Biophys. Res. Commun., 1975, 66, 1316), to give the derivatives of formula (7). The selective acylation of the primary hydroxyl at the 6 position of the saccharide residue can then be done directly, notably by the action of a slight excess of the anhydride of a carboxylic acid. Derivatives of formula (8) are obtained.

The derivatives of formula (8) may be synthesized according to a totally different sequence (diagram II), formula (4) similar to that developed by KUSUMOTO et al. (Tetrahedron Letters, 1976, 47, 4237), from the specific tosylation of the primary alcohol of the saccharide residue.

In another modification, the derivatives of formula (7) are deacylated on both hydroxyls at the 4 and 6 position of the saccharide residue, notably by the action of an excess of the anhydride of a carboxylic acid to give compounds of formula (9).

In a modification for which the carboxyl function of the D-glutamine residue is free ($R_7$=OH) in the derivatives of formula (5), (7), an ester group ($R_7$) is introduced a posteriori according to the technique of WANG et al. (J. Org. Chem., 42, 1977, 1286), to produce derivatives of formulae (6), (8) and (9) (Diagram I). The same reaction sequence is applicable to the production of derivatives of formula (4), (Diagram II).

DIAGRAM (I)
SYNTHESIS SEQUENCES OF GLYCOPEPTIDE COMPOUNDS

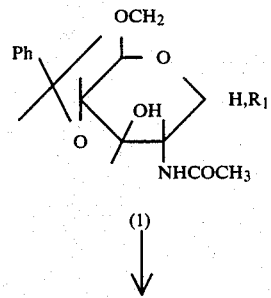

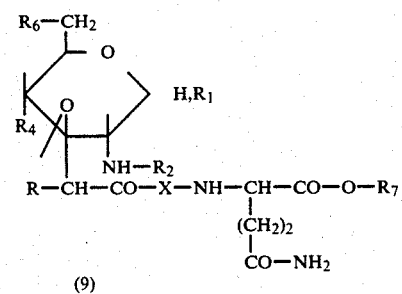

DIAGRAM (I)
SYNTHESIS SEQUENCES OF GLYCOPEPTIDE COMPOUNDS

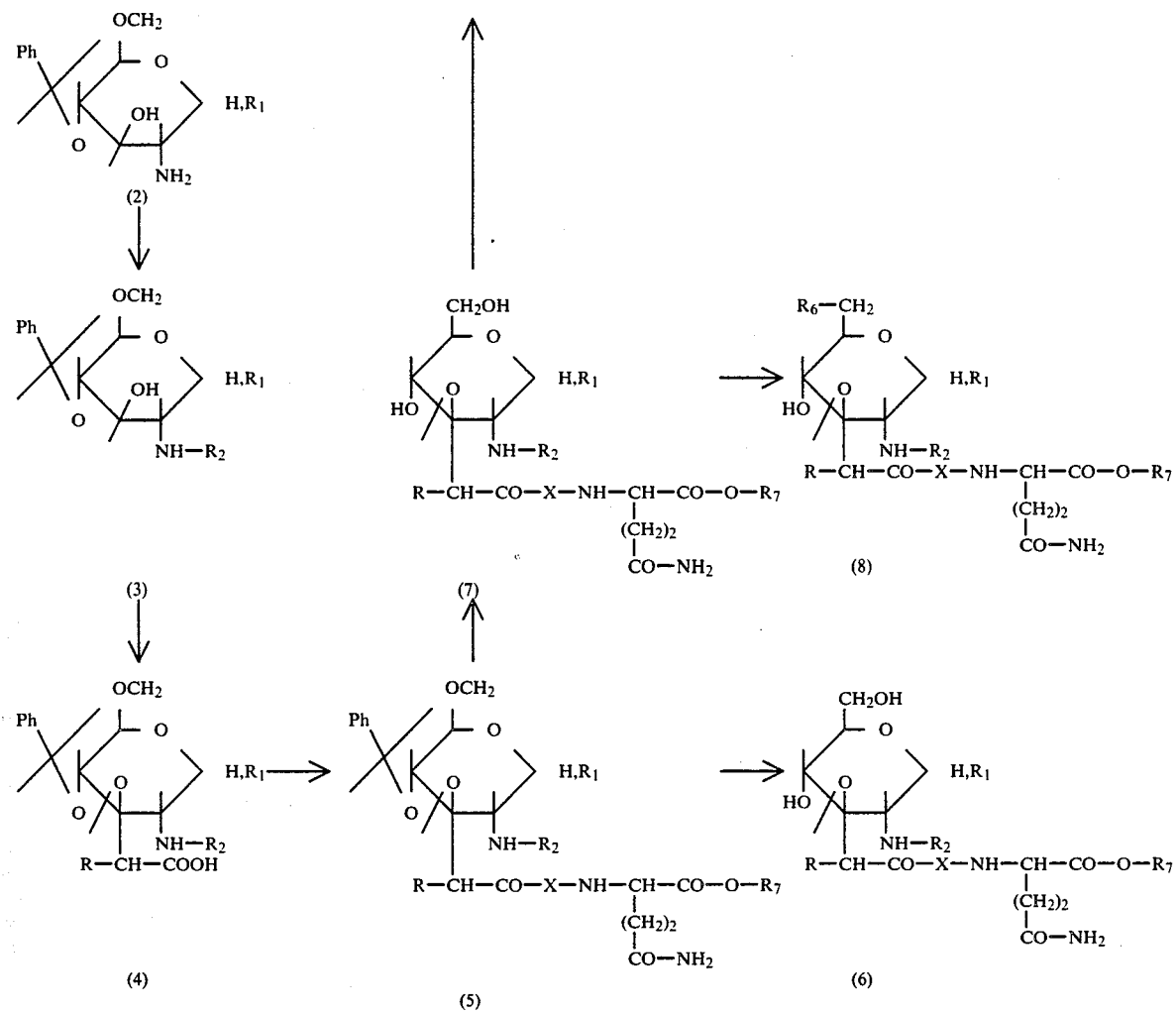

DIAGRAM (II)
SYNTHESIS SEQUENCE OF THE GLYCOPEPTIDE DERIVATIVES CORRESPONDING TO THE GENERAL FORMULA AND OF WHICH THE HYDROXYL AT THE C6 POSITION OF THE SACCHARIDE RESIDUE IS ACYLATED BY A LONG CHAIN FATTY ACID

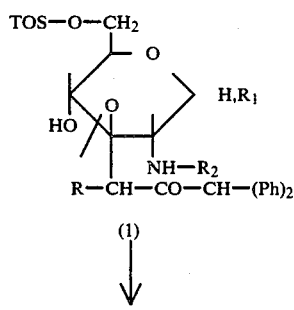

-continued
DIAGRAM (II)
SYNTHESIS SEQUENCE OF THE GLYCOPEPTIDE DERIVATIVES CORRESPONDING TO THE GENERAL FORMULA AND OF WHICH THE HYDROXYL AT THE C6 POSITION OF THE SACCHARIDE RESIDUE IS ACYLATED BY A LONG CHAIN FATTY ACID

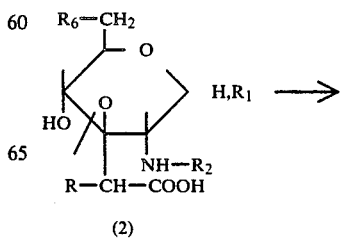

-continued
DIAGRAM (II)
SYNTHESIS SEQUENCE OF THE GLYCOPEPTIDE
DERIVATIVES CORRESPONDING TO THE GENERAL
FORMULA AND OF WHICH THE HYDROXYL AT THE C6
POSITION OF THE SACCHARIDE RESIDUE IS
ACYLATED BY A LONG CHAIN FATTY ACID

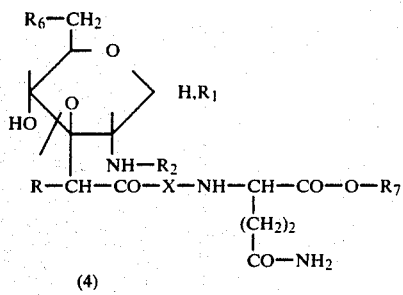

(4)

The invention also relates to methods of utilization of the compounds corresponding to the foregoing definition, notably as a reactant or as active substance in pharmaceutical compositions.

The invention relates to biological reactants, for example, standard immunological adjuvants, which can be constituted by means of the compounds according to the invention, notably in order to study the possible adjuvant properties of substances under investigation, by comparison with such standard adjuvants, or on the contrary, as an agent capable of opposing certain effects connected with the administration of immunosuppressive substances.

More particularly, the invention relates to medicaments including as active principle at least one of the compounds according to the invention, this medicament being applicable as regulator of the immune response of the subject to whom it is administered.

These medicaments are notably applicable when a reinforcement of the immune response to any immunogenic agent is sought. Such immunogenic agents can be natural or synthetic and necessitate the use of an agent stimulating the immunitary system, whether the immunogenic agent is weak in nature, or whether it is strong and can be used at a very low dose, or again if the immunogenic character has been reduced, for example in the course of prior modifications or purifications. Generally, the use of immunoregulator compounds according to the invention is useful any time that the immunogenic agent does not permit the induction of a sufficient response.

The invention relates more particularly also to the use of the compounds concerned in amplifying the immunogenic effect of active principles of vaccines administered to an animal or human host, notably in the case where these vaccinating principles being to the categeries of immunogenic agents recalled above. Consequently, the invention relates equally to pharmaceutical compositions also whose active principle is constituted by at least one of the compounds according to the invention, in association with the suitable pharmaceutical vehicles for the mode of administration required or usable having regard to the nature of the vaccinating principle used.

The invention applies in particular to those vaccinating agents whose immunogenic character is strong but which are difficult to use normally by reason of too high toxicity or undesirable secondary effects. It has been confirmed that the adjuvant agent according to the invention were capable of compensating effectively for the loss in the immunogenic effect which would result normally from dilution or reduction of the doses used, notably for the purpose of reducing the toxicity or the secondary effects above-mentioned to a corresponding proportion, and this without unfavorably influencing the latter phenomena.

The same effects are observed in the case of strong vaccinating agents of which the immunogenic character has been reduced, notably by extensive purification, to the extent that this appears necessary in the corresponding decrease of their toxic or troublesome side effects. Such is the case in particular with vaccinating principles constituted by bacterial or viral anatoxins or, generally, vaccinating principles constituted by a part only of the constituents initially contained in the bacteria or virus against which protection is sought.

In a general way, the invention applies to any antigen which has undergone chemical or physical transformations seeking to eliminate or modify the parts of the antigen which are responsible for its troublesome secondary effects whilst preserving the parts which are the source of its immunogenic properties. It is to this type of weak immunogen that are attached for example the principles constituted by the "sub-units" derived from flu virus, and which only retain the hemagglutinins and neuraminidases of the latter, to the exclusion of the nucleoproteins and other nucleotide constituents of the virus from which they are derived. This applies equally to certain anatoxins, such as those, for example, of diphtheria or tetanus, which, it is known, can be constituted by soluble substances, such as obtained by the simultaneous action of formaldehyde and heat on bacterial toxins derived from the corresponding bacteria.

The invention relates again to the application of the compounds according to the invention, and notably of those for which $R_7$ contains 4 carbon atoms or more, for the treatment of infectious diseases. In this application, it must be noted that the products according to the invention are clearly distinguished from the antibiotics habitually used. The products according to the invention, contrary to antibiotics, do not have a bacteriocidal or bacteriostatic effect on in vitro. On the contrary, they can activate the macrophages isolated in vitro and their action in vivo is manifest as is seen in the examples of the pharmacological trials. Contrary to the antibiotics again, the action is not limited to certain varieties of micro-organisms. This is explained by the fact that their activity is not direct but is developed through non-specific immune defense mechanisms of the host, which mechanisms are stimulated and magnified by their administration. This difference in action with respect to the antibiotics renders these products all the more advantageous in that they can be used against pathogenic germs which have become resistant to antibiotics.

The mode of action of the products according to the invention likens them to the known anti-infectious compounds such as OCB or lipopolysaccharides and as such may be employed with success for the treatment of infections without presenting the drawbacks, notably of toxicity, which limit or forbid the use of the LPS or of CGB.

The products according to the invention may in particular be used to combat non-spedifically diseases caused by micro-organisms such as Klebsiella, Pseudomonas, staphylococci, etc.

The applications indicated previously by way of examples are not exclusive of other applications bringing into play the immunoregulator properties of the compounds according to the invention. It is possible also to cite by way of example their reinforcing action at the level of the specific immunization of the host with regard to parasitic antigens, the restoration of the immunocompetence of the host, when the latter is at a lower level than normal, notably when the latter has been damaged by antigens or parasites themselves, or under the effect of chemotherapy, of radiotherapy, or of any other treatment which has an immunosuppressive action.

The pharmaceutical compositions according to the invention, generally, are useful for the treatment or the prevention of infectious diseases of bacterial or parasitic origin, or for the inhibition of tumoral disorders.

The adjuvants according to the invention may be administered to the host-animal or human being in any suitable manner to obtain the desired effect. The administrations of the immunoregulator principle, notably adjuvant, and of the immunogenic agent, notably of vaccinating antigen, may be envisaged simultaneously or separately, in the latter case if necessary staggered in time, possibly also by similar or different routes of administration (for example parenteral and oral routes respectively or vice versa).

The invention relates naturally also to the various pharmaceutical compositions with which the compounds according to the invention may be incorporated, if necessary in association with other active substances. In particular, the compounds I are advantageously associated with immunogenic agents, whether they are for example immunogenic agents used at very low doses, or weak immunogenic agents.

Advantageous pharmaceutical compositions are constituted by injectable solutions, suspensions or liposomes containing an effective dose of at least one product according to the invention. Preferably, these solutions suspensions or liposomes are formed in an isotonic sterilized aqueous phase, preferably saline or glucosed.

The invention relates more particularly to such suspensions, solutions or liposomes which are suitable for administration by intradermal, intramuscular or subcutaneous injection, or again by scarification.

It relates also to pharmaceutical compositions administerable by other routes, notably by the oral or rectal route, or again in the form of aerosols designed to come into contact with the muscous membranes, notably the ocular, nasal, pulmonary or vaginal mucous membranes.

Consequently, it relates to pharmaceutical compositions in which one at least of the compounds according to the invention is associated with pharmaceutically acceptable excipients, solid or liquid, adapted for the constitution of oral, ocular or nasal forms, or with excipients adapted for the constitution of rectal forms of administration, or again with gelatinous excipients for vaginal administration. It relates also to isotonic liquid compositions containing one at least of the products according to the invention, adapted for administration to the mucous membranes, notably the ocular or nasal mucous membranes. It relates finally to compositions formed from pharmaceutically acceptable liquefied gases, of the "propellant" type, in which the products according to the invention are dissolved or held in suspension, and whose release causes dispersion in an aerosol.

The invention consists also of a method of treatment aimed at reinforcing the immune defenses of the host, consisting of administering to the latter an effective dose of one at least of the products according to the invention, in one of the administrative forms which have been mentioned above. By way of example of doses capable of inducing an effect, may be mentioned doses of 10 to 1,000 μg per kg of body weight, for example, 50 μg, when the administration is effected by the parenteral route, or again a dose of 200 to 20,000 μg per kg of body weight, for example, 1,000 μg, for other modes of administration, such as for example the oral route.

Other characteristics of the invention will appear in the course of the description of the examples of the preparation of products according to the invention as well as of the tests establishing the properties of these products, which follows.

The abbreviations used in this description have the following significances:
Ala: alanine
Gln: glutamine
Mur-NAc: N-acetyl-muramic acid
BOC: t-butyloxycarbonyl
OMe: methyl ester
OBu: butyl ester
OSu: succinimide ester
Bzl: benzyl
Bzi: benzylidene
Z: benzyloxycarbonyl (1) Synthesis of the methyl ester of N-acetyl-muramyl-L-alanyl-D-glutamine (a) t-butyloxycarbonyl of the methyl ester of D-glutamine BOC-D-Gln-OMe (I)

1.5 g (6.1 mmoles) of t-butyloxycarbonyl-D-glutamine (BOC-D-Gln), prepared by the method described by SCHN/BEL (Liebigs, Ann. Chem. (1967) 702, 188–196), are dissolved in 60 ml of absolute methanol. At 0° C., is added drop by drop an ether solution of diazomethane until the persistance of the yellow color. The reaction mixture is allowed to stand with stirring at 0° C. for 10 minutes, then at ordinary temperature for a similar time. The progress of the reaction is checked by chromatography on a thin layer of silica gel in the solvent systems n-butanol-acetic acid-water (4:1:5 upper phase), n-butanol-pyridine-acetic acid-water (30:20:6:24) and chloroform-methanol (5:1). The excess of diazomethane is destroyed by the addition of glacial acetic acid and the reaction mixture is concentrated to dryness. The residue is taken up in a minimum of ethyl acetate and precipitated with petroleum ether. Its melting point is 86°–90° C. and its rotatory power $[\alpha]_D^{25} = +24.7°$ (methanol).

1.417 g of BOC-D-Gln-OMe are obtained, namely a yield of 89.7%.

The elementary analysis of this product is for $C_{11}H_{20}N_2O_5$ (260.29)

|             | C     | H    | N     |
|-------------|-------|------|-------|
| calculated: | 50.76 | 7.75 | 10.76 |
| found:      | 50.62 | 7.75 | 10.82 |

(b) Hydrochloride of the methyl ester of D-glutamine HCl, D-Gln-OMe (II)

1.4 g (5.4 mmoles) of (I) are treated with 15 ml of a normal solution of hydrochloric acid in glacial acetic acid. After 30 minutes at ordinary temperature, the reaction mixture is concentrated to dryness and the oil obtained is dried under vacuum in the presence of KOH.

(c) Methyl ester of t-butyloxycarbonyl-L-alanyl-D-glutamine BOC-L-Ala-D-Gln-OMe (III)

1.86 g (6.5 mmoles) of succinimide ester of t-butyloxycarbonyl-alanine (BOC-Ala-OSu), prepared according to ANDERSON et al. (J. Am. Chem. Soc. (1964) 86, 1839–1842), are added to a solution of 1.2 g (5.4 mmoles) of (II) and of 0.6 ml (5.4 mmoles) of N-methylmorpholine in 25 ml of dimethylformamide. After one night at ordinary temperature, the reaction mixture is concentrated to dryness and chromatographed on a silica column (27×3 cm), pre-equilibrated in the system chloroform-isopropanol-acetic acid (100:0.5:0.2), by elution with the system chloroform-isopropanol-acetic acid (100:5:2). The fractions containing the product are combined and concentrated to dryness. By crystallization in the mixture isopropanol-isopropyl ether, 1.035 g of (III) are obtained. Its melting point is 115°–116° C. and its rotatory power $[\alpha]_D^{25} = -9°$ (methanol).

The elementary analysis of this product is for $C_{14}H_{25}N_3O_6$ (331.37)

|  | C | H | N |
|---|---|---|---|
| calculated: | 50.74 | 7.60 | 12.68 |
| found: | 50.79 | 7.40 | 12.42 |

(d) Hydrochloride of the methyl ester of L-alanyl-D-glutamine HCl, L-Ala-D-Gln-OMe (IV)

332 mg (1 mmole) of (III) are treated with 3 ml of a normal solution of hydrochloric acid in glacial acetic acid. After 30 minutes at ordinary temperature, the reaction mixture is concentrated to dryness and the oil obtained is dried under vacuum in the presence of KOH.

(e) Coupling of the peptide derivative (IV) with the protected derivative of the muramyl residue (1-α-Bzl-4,6-Bzi)-Mur-NAc-L-Ala-D-Gln-OMe (V)

471.5 mg (1 mmole) of (1-α-Bzl-4,6-Bzi)-Mur-NAc, prepared according to OSAWA and JEANLOZ (J. Org. Chem. (1965) 30, 488), are dissolved in 5 ml of dimethylformamide containing 0.11 ml (1 mmole) of N-methylmorpholine. To this solution cooled to −15° C. is added 0.13 ml (1 mmole) of isobutyl chloroformate. After 3 to 5 minutes, a solution, cooled to −15° C., of 268 mg (1 mmole) of (IV) and of 0.11 ml (1 mmole) of N-methylmorpholine in 5 ml of dimethylformamide is added to the preceding solution. After one night at −15° C., 1 ml of a 2.5M solution of potassium carbonate is added. After 30 minutes at 0° C., the product is precipitated by the addition of water to the reaction mixture, filtered, washed on the filter with a molar solution of potassium bicarbonate and dried under vacuum in the presence of $P_2O_5$. 620 mg (90.5%) of the product (V) are obtained. Its melting point is 215°–220° C. and its rotatory power $[\alpha]_D^{25} = +92.6°$ (dimethylformamide).

(f) Methyl ester of N-acetyl-muramyl-L-alanyl-D-glutamine Mur-NAc-L-Ala-D-Gln-OMe (VI)

587.6 mg (0.86 mmole) of (V), dissolved in 35 ml of glacial acetic acid, are hydrogenated for 60 hours in the presence of 450 mg of 5% palladium on charcoal. After filtration of the catalyst, the acetic acid is removed under vacuum. The product is taken up again in an 0.1M acetic acid solution, deposited on an ion exchange resin column (10×1 cm) marketed under the name "Amberlite AG 50 W-X 2", and eluted with the same acetic solution. After freeze-drying the eluate containing the product, the same procedure is followed for chromatography of the product on "Amberlite AG 1 X-2" resin. Finally 290 mg of the freeze-dried product are obtained.

This product is chromatographed on a silica column previously equilibrated in the mixture n-butanol-acetic acid-water (65:10:25). The same mixture is used for the elution of the product. The fractions containing the pure product are combined, extracted with water, and the aqueous phase obtained is freeze-dried. 235.4 mg of the product are obtained. Its melting point is 108°–112° C. and its rotatory power $[\alpha]_D^{25} = +34.3°$ (glacial acetic acid).

Elementary analysis of the product is as follows for $C_{20}H_{34}N_4O_{11} \cdot 1.25\ H_2O$ (529.02)

|  | C | H | N |
|---|---|---|---|
| calculated: | 45.40 | 6.95 | 10.59 |
| found: | 45.46 | 6.76 | 10.56 |

(2) Synthesis of the n-butyl ester of N-acetyl-muramyl-L-alanyl-D-glutamine (a) Z-Ala-D-Gln (I)

2.4 g (16.4 mM) of D-glutamine are solublized hot in 35 ml of water. At room temperature, 2.3 ml (16.4 mM) of triethylamine and 4.62 g (14.4 mM) of Z-L-Ala-OSu, in solution in 70 ml of anhydrous tetrahydrofuranne (THF) are added. The reaction occurs at 4° C. over 48 hours. 0.5 ml (3.85 mM) of dimethylaminopropylamine are added.

After 1 hour at ordinary temperature, the reaction mixture is diluted by 65 ml of water, then acidified at pH 2.2–3 with 4N HCl, at 0° C. The THF is removed under vacuum.

The product precipitates. After one night at 4° C., it is filtered and washed with a minimum of iced water. It is crystallized in ethanol between hot and cold.

2.85 g of product are obtained, namely a yield of 62%. Its melting point is 179°–182° C., and its rotatory power $[\alpha]_D^{20} = -13.3°$ (methanol).

The elementary analysis thereof is: for $C_{16}H_{21}N_3O_6$ (351.37)

|  | C | H | N |
|---|---|---|---|
| calculated: | 54.69 | 6.02 | 11.96 |
| found: | 54.18 | 5.8 | 11.77 |

(b) Z-Ala-D-Gln-O-n-Bu (II)

350 mg (1 mM) of (I), dissolved in 15 ml of THF and 5 ml of $H_2O$, are converted into cesium salt by addition of a 20% aqueous solution of $Cs_2CO_3$ (1 mM). After concentration to dryness, then drying by evaporation with dimethylformamide, several times, and by dessication under vacuum (dessicator with $P_2O_5$), the dry residue is dissolved in 30 ml of dimethylformamide, and 0.12 ml (1.1 mM) of 1-bromo-n-butane added.

After 20 hours, a check is made, by thin layer chromatography on silica gel in the system acetate-pyridine-acetic acid-water (6:2:0.6:1), that the reaction is completed. If not, 0.06 ml (0.55 mM) of 1-bromo-n-butane are again added and it is allowed to react for a further 20 hours. The reaction mixture is then concentrated to the minimum and the product precipitated with water.

332 mg of product are obtained, namely a yield of 81.5%. Its melting point is 148°–150° C.

The elementary analysis thereof is: for $C_{20}H_{29}N_3O_6$ (407.47)

|  | C | H | N |
|---|---|---|---|
| calculated: | 58.95 | 7.17 | 10.31 |
| found: | 58.91 | 7.12 | 10.26 |

(c) L-Ala-D-Gln-O-n-Bu (III)

330 mg (0.8 mM) of (II), dissolved in 30 ml of glacial acetic acid, are hydrogenated for 4 hours, in the presence of 330 mg of Pd (5%) on charcoal and of 1 ml (1 mM) of N HCl. It is checked, by thin layer chromatography on silica gel in the system ethyl acetate-pyridine-acetic acid-water (6:2:0.6:1), that the hydrogenation is complete, then the catalyst is filtered off and the solvent concentrated. The residual oil is dried carefully under vacuum (dessicator, with $P_2O_5$) and used as such in the following step.

254 mg of product, namely a yield of 100%, is obtained.

(d) Mur-NAc(1-bzl-4,6-O-Bzi)-L-Ala-D-Gln-OBu (IV)

The preparation of this derivative is carried out conventionally by the mixed anhydride method.

Starting from 0.9 mM of Mur-NAc(1-bzl-4,6-O-Bzi) and 0.8 mM of (III), a yield of 81.2% is obtained. The melting point of the product is 220°–235° C. and its rotatory power $[\alpha]_D^{20} = +82.6°$ (dimethylformamide).

The elementary analysis of the product is: for $C_{37}H_{50}N_4O_{11}$ (726.84)

|  | C | H | H |
|---|---|---|---|
| calculated: | 61.14 | 6.93 | 7.71 |
| found: | 61.77 | 7.03 | 7.03 |

(e) Mur-NAc-L-Ala-D-Gln-O-n-Bu (V)

472 mg (0.6 mM) of (IV), dissolved in 30 ml of glacial acetic acid, are hydrogenated for 40 hours, in the presence of 470 mg of Pd (5%) on charcoal. After chromatographic checking on a silica gel plate in the system $CHCl_3$—MeOH (50–15), the catalyst is filtered off and the filtrate concentrated.

The oily residue is taken up again in $CHCl_3$—MeOH (50:15) and chromatographed on a silica 60 column (33 g) with $CHCl_3$—MeOH (50:15). The fractions containing the product are concentrated to dryness; the residue is taken up again in water, then freeze-dried after ultra-filtration.

157 mg of product are obtained, namely a yield of 48%. Its rotatory power is $[\alpha]_D^{20} = +34.8°$ (acetic acid).

The elementary analysis of the product is: for $C_{23}H_{40}N_4O_{11} \cdot \frac{1}{3} H_2O$

|  | C | H | N |
|---|---|---|---|
| calculated: | 48.24 | 7.50 | 9.78 |
| found: | 48.26 | 70.8 | 9.74 |

(3) Synthesis of the n-decyl ester of N-acetyl-muramyl-L-alanyl-D-glutamine (a) This product is prepared by the method described above for the n-butyl ester of N-acetyl-muramyl-L-alanyl-D-glutamine.

The product obtained under these conditions has a rotary power of $[\alpha]_D^{20} = +30°$ (glacial acetic acid).

Its elementary analysis is: for $C_{29}H_{52}N_4O_{11}$—0.15 $CHCl_3$ (650.64)

|  | C | H | N |
|---|---|---|---|
| calculated: | 53.81 | 8.08 | 8.61 |
| found: | 53.97 | 8.06 | 8.47 |

(b) The same product was synthesized by a second sequence.

492.5 mg (1 mM) of Mur-NAc-L-Ala-D-Gln, dissolved in 15 ml of THF and 5 ml of $H_2O$, were converted into cesium salt by the addition of a 20% aqueous solution of $Cs_2CO_3$ (1 mM). After concentration to dryness, then drying by evaporation with dimethylformamide, several times, and by dessication, the residue is dissolved in 30 ml of dimethylformamide, and 0.13 ml (1.1 mM) of 1-bromo-n-decane added. After 20 hours, the reaction mixture is concentrated to dryness. The product, after chromatography on silica column in the mixture chloroform-methane (50:15), is obtained by precipitation in methanol-ether.

Its rotatory power is $[\alpha]_D^{20} = +29°$ (glacial acetic acid).

The elementary analysis of the product is: for $C_{29}H_{52}N_4O_{11}$—0.25 $CHCl_3$ (661.9)

|  | C | H | N |
|---|---|---|---|
| calculated: | 53.08 | 7.96 | 8.47 |
| found: | 53.2 | 8.0 | 8.50 |

(4) Synthesis of n-propyl ester of N-acetyl-muramyl-L-alanyl-D-glutamine

The product prepared by the method described for the n-butyl ester of N-acetyl-muramyl-L-alanyl-D-glutamine.

The rotatory power of the product obtained is $[\alpha]_D^{20} - +32.3$ (glacial acetic acid).

(5) Synthesis of the n-hexyl ester of N-acetyl-muramyl-L-alanyl-D-glutamine

The product is prepared by the method described for the n-butyl ester of N-acetyl-muramyl-L-alanyl-D-glutamine.

The rotatory power of the product obtained is $[\alpha]_D^{20} = +29.5$ (glacial acetic acid).

Pharmacological properties (1) Toxicity

The toxicity of the products according to the invention were studied by parenteral administration notably in the rabbit. It is observed that the toxic doses are of an order of magnitude very much higher than that of the doses at which these products manifest their activity. Thus, these products are well tolerated in the rabbit at doses equal to or greater than 5 mg/kg of animal.

(2) Pyrogenicity

In the course of tests on rabbits, the maximum temperature variations during the three hours following administration were followed. For doses as high as 5 mg/kg or more of product, no significant variation in temperature is observed. Thus the average rise in temperature for administration to rabbits, for different esters of Mur-NAc-L-Ala-D-Gln is:

| | | |
|---|---|---|
| methyl ester | at 5 mg/kg | 0.53° C. |
| butyl ester | at 10 mg/kg | 0.30° C. |
| decyl ester | at 10 mg/kg | 0.23° C. |

It can hence be considered that, at active doses as emerge from the tests reported below, this product is completely apyrogenic.

(3) Adjuvant character in the aqueous phase

In this series of trials of which the results are indicated below, the influence of the active principle according to the invention on the level of anti-albumin antibodies under the following conditions, were studied.

Groups of 8 Swiss mice aged two months received, by sub-cutaneous injection, 0.5 mg of antigen constituted by bovine serum albumin (BSA) with or without the tested substance in isotonic saline solution. This high dose of antigen, because it is situated at the limit of the paralysing dose with respect to the immune response, results for this reason, in a weak or nil response to the antigen alone in the controls; it therefore constitutes a severe criterion for establishing the activity of an adjuvant substance. Thirty days later, the mice received, by the same route of administration, a booster containing 0.1 mg of the same antigen.

By way of comparison, the adjuvant effect was studied simultaneously of 2-(2-acetamido-2-deoxy-3-O-D-glucopyranosyl)-D-propionyl-L-alanyl-D-isoglutamine (MDP) known for its adjuvant properties.

The antibody level is determined by passive hemagglutination using sheep's red blood cells treated with formalin and covered with the antigen studied according to the method described by A. A. HIRATA and M. W. BRANDISS (J. Immunol., 100, 641–648, 1968). Samples were taken respectively after the first injection of antigen and after injection of the booster to determine the primary and secondary responses.

The results of these tests are given in the following table. The antibody titers express the maximum serum dilution agglutinating a given amount of sheep's red blood cells.

TABLE 1

| | Antibody Titer | |
|---|---|---|
| | Primary Response | Secondary Response |
| BSA Controls | <3 | 16 ± 16 |
| BSA + MDP 100 µg | 50 | 300 ± 100 |
| BSA + Mur—NAc—L-Ala—D-Glu(NH$_2$)—OCH$_3$ 100 µg | 100 | 500 ± 150 |
| BSA + Mur—NAc—L-Ala—D-Glu(NH$_2$)—OC$_4$H$_9$ 100 µ | 12 | 600 ± 200 |
| BSA + Mur—NAc—L-Ala—D-Glu(NH$_2$) 100 µg | 25 | 200 ± 90 |

These results show that the methyl and butyl esters, administered in isotonic saline solution, cause a considerable increase in the level of antibodies formed. The effect appears even greater than that that is observed in the subjects treated with MDP.

(4) Adjuvant character of Mur-NAc-L-Ala-D-Glu(NH$_2$)—OCH$_3$ in the presence of an oily phase In these tests, the growth of the specific antibody level of a given antigen is followed when the latter is injected, with or without the adjuvant compound according to the invention, in a water in oil emulsion.

The tests were carried out on batches of 6 female Hartley guinea pigs of 350 g. The administration was done by intradermal injection into the plantar pad of each of the rear paws. The ovalbumin (constituting the antigen) at the dose of 1 mg is prepared in 0.1 ml of a saline isotonic solution emulsion, in an oily phase constituted by the Freund incomplete adjuvant (FIA). The compound according to the invention is administered at the dose of 0.1 mg added in the emulsion containing the FIA.

As previously, by way of comparison, a test was carried out with MDP in place of the product according to the invention.

Eighteen days after this immunization, possible reactions are sought of delayed hypersensitivity to the antigen by injecting by the intradermal route 0.01 mg of ovalbumin into the side of the animals, and there was observed, 48 hours later, the reaction at the point of injection. The diameter in millimeters of the reaction thus-caused was measured.

Twenty-one days after the injection, the animals were bled. In the serum collected, the content is measured of specific antibodies of ovalbumin by precipitation of the antibody-antigen complex in the equivalence zone. The amount of protein nitrogen contained in this precipitate was estimated by the method of Folin. The average values of the contents of antibodies are indicated in the table of results. These values express the amount, in micrograms, of nitrogen precipitatable by the antigen, per millimeter of serum.

The results of these tests are reported in the following Table 2.

TABLE 2

| Composition of the emulsion containing the antigen | Serum Antibodies (µg/ml) | Cutaneous test (diameter in mm) |
|---|---|---|
| FIA | 800 | 0 |
| FIA + MDP (100 µg) | 5,000 | 15 |
| FIA + Mur—NAc—L-Ala—D-Glu (NH$_2$)—OCH$_3$ (100 µg) | 6,000 | 17 |
| FIA + Mur—NAc—L-Ala—D-Glu (NH$_2$)—OC$_4$H$_9$ | 2,000 | 8 |

These results show that the methyl and butyl esters administered in an oily emulsion, enable a very considerable increase in the level of antibodies formed in response to the injection of the antigen, and that it induces a delayed hypersensitivity reaction to with respect to the same antigen, these two reactions being at least equal to those observed with MDP.

(5) Anti-infection activity with respect to Klebsiella

The testing procedure is described in the article CHEDID L. et col., Proc. Natl. Acad. Sci. USA 1977, 74: 2089.

An experimental method is thus established previously enabling the anti-infectious character of the products to be demonstrated. It was shown that a dose of 1 to $2.10^4$ Klebsiella pneumoniae, injected by the intramuscular route to mice, results in the progressive death of a considerable part, if not of the whole, of the animals in the week following inoculation. After eight days, the survival of the remaining animals is finally achieved.

The survival of groups of mice inoculated under the above-indicated conditions and treated by means of the products according to the invention, was followed.

For these tests, hybrid mice (C571B1/6×AKR)F1 raised at the INSTITUT PASTEUR were used, there mice being raised from strains coming from the C.N.R.S. breeding station at ORLEANS.

Infection by *Klebsiella pneumoniae*, capsular type 2, biotype d, strain was effected with a 16 hour culture in medium for pneumococci (No. 53515, INSTITUT PASTEUR) was effected. The infecting dose was $2.10^4$ Klebsiella; it was administered by the intramuscular route.

The administration of the tested product is effected by the intravenous route in 0.2 ml of apyrogenic physiological solution, the controls receiving the solution alone. It is carried out 24 hours before the inoculation.

Under the conditions of these tests, the butyl and decyl esters of Mur-NAc-L-Ala-D-Glu show and anti-infectious activity, which is manifested by a higher percentage of survivors than that of the control group.

TABLE 3

| Product | Number mice D0 | % Survival D3 | D5 | D10 | % Protection |
|---|---|---|---|---|---|
| Controls | 24 | 29 | 12.5 | 12.5 | |
| Mur—NAc—L-Ala—D-Glu(NH₂)—OC₄H₉ | 24 | 92 | 75 | 75 | 63 |

(6) Absence of influence on coagulation mechanisms

It is known, from recent studies, that compounds having adjuvant properties like LPS can have side effects. Thus it has been observed in the rabbits that the administration of LPS has a tendency to shorten the coagulation time. The reasons for this phenomena are not fully known; nonetheless, it has seemed useful to determine the effect of the products according to the invention on coagulation under the same conditions.

For these tests, the test described by LERNER et col. in Thrombosis Research, Vol. 11, pp. 253-261, 1977, "Endotoxin induced disseminated intravascular clotting: evidence that it is mediated by neutrophile production of tissue factor", was used.

The total blood was divided into two portions of which one was centrifuged to obtain platelet-free plasma (PFP).

1 ml of total blood was incubated in a plastic tube in the presence of 100 µg of the product to be tested.

Tubes were also prepared containing 0.1 ml of PFP to which every hour, from 0 to 5 hours, were added 0.1 ml of incubation mixture, then these were recalcified by 0.1 ml of 0.025M calcium chloride.

The coagulation time was noted and the pro-coagulating activity was deduced therefrom as a function of the shortening of the coagulation time with respect to the control, physiological water. The result was compared with that of a highly pro-coagulant reference standard, the LPS.

The results of these tests are shown in the following table. The coagulation times are expressed in seconds.

It is observed that the butyl and methylesters of Mur-NAc-Ala-D-Glu, contrary to LPS, do not accelerate coagulation.

TABLE 4

| Incubation h | Water | LPS | Methyl ester | Butyl ester |
|---|---|---|---|---|
| 0 | 131 | 129 | 125 | 129 |
| 2 | 129 | 118 | 118 | 120 |
| 3 | 122 | 98 | 109 | 122 |
| 4 | 119 | 88 | 110 | 114 |
| 5 | 113 | 77 | 104 | 108 |

We claim:
1. A compound of the formula

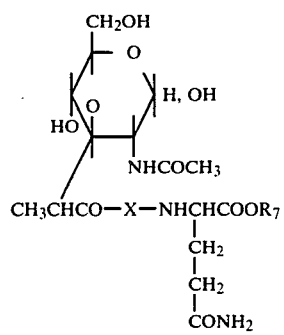

wherein X is selected from the group consisting of L-alanyl, L-seryl and L-valyl;
and $R_7$ is selected from the group consisting of $CH_3$, $C_2H_5$, $C_3H_7$, $C_4H_9$, $C_5H_{11}$, $C_6H_{13}$ and $C_{10}H_{21}$.

2. The compound of claim 1 wherein X is L-alanyl and $R_7$ is $CH_3$.

3. The compound of claim 1 wherein X is L-alanyl and $R_7$ is $C_2H_5$.

4. The compound of claim 1 wherein X is L-alanyl and $R_7$ is $C_3H_7$.

5. The compound of claim 1 wherein X is L-alanyl and $R_7$ is $C_5H_{11}$.

6. The compound of claim 1 wherein X is L-alanyl and $R_7$ is $C_6H_{13}$.

7. The compound of claim 1 wherein X is L-alanyl and $R_7$ is $C_{10}H_{21}$.

8. The compound of claim 1 wherein X is L-valyl and $R_7$ is $C_4H_9$.

9. The compound of claim 1 wherein X is L-seryl and $R_7$ is $C_4H_9$.

10. A biological composition which has an improved therapeutic index and is concurrently an effective adjuvant and virtually apyrogenic, which composition comprises a biologically acceptable carrier and in a biologically effective amount, a compound of the formula

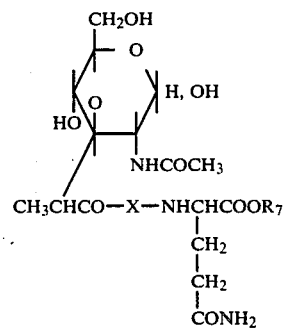

wherein X is selected from the group consisting of L-alanyl, L-seryl and L-valyl;
and $R_7$ is selected from the group consisting of $CH_3$, $C_2H_5$, $C_3H_7$, $C_4H_9$, $C_5H_{11}$, $C_6H_{13}$ and $C_{10}H_{21}$.

11. The biological composition of claim 10 wherein the compound is N-acetyl-muramyl-L-alanyl-D-glutamine n-butyl ester.

12. The biological composition of claim 10 wherein the compound is N-acetyl-muramyl-L-alanyl-D-glutamine-methyl ester.

13. A therapeutic method which comprises administering to a host consisting of an animal or human in an effective amount a composition of claim 10 to stimulate an immunological response, while virtually causing no pyrogenicity to said host.

14. The therapeutic method of claim 13 wherein the compound in the composition is N-acetyl-muramyl-L-alanyl-D-glutamine n-butyl ester.

15. The therapeutic method of claim 13 wherein the compound in the composition in N-acetyl-muramyl-L-alanyl-D-glutamine methyl ester.

16. A biological composition which has an improved therapeutic index and is concurrently an effective adjuvant, is anti-infectious and virtually apyrogenic, which composition comprises a biologically acceptable carrier and in a biologically effective amount, a compound of the formula

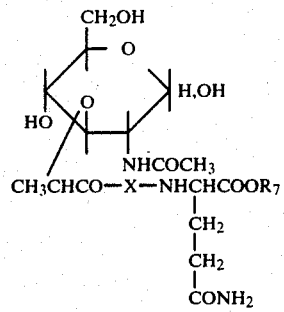

wherein X is selected from the group consisting of L-alanyl, L-seryl and L-valyl;
and $R_7$ is selected from the group consisting of $C_4H_9$, $C_5H_{11}$, $C_6H_{13}$ and $C_{10}H_{21}$.

17. The biologically composition of claim 16 wherein the compound is N-acetyl-muramyl-L-alanyl-D-glutamine n-butyl ester.

18. A therapeutic method which comprises administering to a host consisting of an animal or human in an effective amount a composition of claim 16 to stimulate an immunological and an anti-infectious response, while virtually causing no pyrogenicity to said host.

19. The therapeutic method of claim 18 wherein the compound in the composition is N-acetyl-muramyl-L-alanyl-D-glutamine n-butyl ester.

20. N-acetyl-muramyl-L-alanyl-D-glutamine n-butyl ester.

* * * * *

UNITED STATES PATENT AND TRADEMARK OFFICE
CERTIFICATE OF CORRECTION

PATENT NO. : 4,693,998
DATED : Sep. 15, 1987
INVENTOR(S) : Pierre Lefrancier et al It is certified that error appears in the above-identified patent and that said Letters Patent is hereby corrected as shown below:

Title page:

[30] Foreign Application Priority Data:

delete "79 16793" and replace by --78 16793--.

Signed and Sealed this

Twelfth Day of September, 1989

*Attest:*

DONALD J. QUIGG

*Attesting Officer*   *Commissioner of Patents and Trademarks*